United States Patent [19]
Lohrmann et al.

[11] Patent Number: 5,660,815
[45] Date of Patent: Aug. 26, 1997

[54] WATER SOLUBLE FLUORINATED FATTY ACID SULFONATE DERIVATIVES USEFUL AS MAGNETIC RESONANCE IMAGING AGENTS

[75] Inventors: Rolf Lohrmann, La Jolla; Ashwin Krishnan, San Diego, both of Calif.

[73] Assignee: Molecular Biosystems, Inc., San Diego, Calif.

[21] Appl. No.: 431,058

[22] Filed: Apr. 28, 1995

[51] Int. Cl.$^6$ .......................... A61K 49/00; G01N 31/00; G01N 33/48
[52] U.S. Cl. .......................... 424/9.37; 424/1.89; 424/9.3; 562/30; 562/1
[58] Field of Search .......................... 424/1.11, 9.1, 424/9.3, 9.37, 1.65, 1.81, 1.85, 1.89, 9.4, 9.5, 400; 562/1, 30

[56] References Cited

U.S. PATENT DOCUMENTS

| | | |
|---|---|---|
| 4,612,185 | 9/1986 | Dean . |
| 4,639,364 | 1/1987 | Hoey . |
| 4,838,274 | 6/1989 | Schweighardt . |
| 4,913,853 | 4/1990 | Hoey . |
| 4,960,815 | 10/1990 | Moos . |
| 5,070,213 | 12/1991 | Huang . |
| 5,081,304 | 1/1992 | Moos . |
| 5,116,599 | 5/1992 | Rogers et al. . |
| 5,130,119 | 7/1992 | Blaszkiewicz et al. . |
| 5,210,290 | 5/1993 | Gries et al. .......................... 562/430 |
| 5,234,680 | 8/1993 | Rogers et al. . |
| 5,248,498 | 9/1993 | Neumann et al. . |
| 5,318,770 | 6/1994 | White et al. . |
| 5,324,504 | 6/1994 | Rogers, Jr. et al. . |
| 5,362,477 | 11/1994 | Moore et al. . |
| 5,385,724 | 1/1995 | White et al. . |
| 5,397,563 | 3/1995 | Rogers . |
| 5,401,493 | 3/1995 | Lohrmann . |

FOREIGN PATENT DOCUMENTS

| | | |
|---|---|---|
| 0250955 | 1/1988 | European Pat. Off. . |
| 0592306 | 4/1994 | European Pat. Off. . |
| 0603403 | 6/1994 | European Pat. Off. . |
| 5-186372 | 7/1993 | Japan . |
| 6-136347 | 5/1994 | Japan . |
| 622246 | 3/1981 | Switzerland . |
| WO 89/03693 | 5/1989 | WIPO . |

OTHER PUBLICATIONS

McBee et al., "A Grignard Reagent from 3–Chloro–1,1, 1–trifluoropropane" *J. Am. Chem. Soc.* (1948) 70:2910–2911.

Runge, Val M., "Magnetic resonance contrast agents" *The Contrast Media Manual*, Williams & Wilkins (1992) Chapter 13, pp. 143–160.

Long et al., "An Overview of perfluoroctylbromide —application as a synthetic oxygen carrier and imaging agent for x–ray, ultrasound and nuclear magnetic resonance" *Biomat., Art, Cells, Art, Org.* (1988) 16(1–3):411–420.

Kimura et al., "Preparation and surface–active properties of sulfopropylated N–alkylperflurooctanamides" *J. Am. Oil Chem. Soc.* (1984) 61(1):105–107.

Knorr et al., "The influence of the aminosulfonic acid taurine on the efficacy of digoxin and ouabain in the guine–a–pig atrium" *Arch. de Farmacol. y Toxicol.* (1981) 7(3):291–306.

Maxwell, "New techniques in the pharmacokinetic analysis of cancer drugs III nuclear magnetic resonance" *Cancer Surveys* (1993) 17:415–423.

*Primary Examiner*—John Kight
*Assistant Examiner*—Dameron L. Jones
*Attorney, Agent, or Firm*—Morrison & Foerster

[57] ABSTRACT

The present invention relates to improved imaging agents useful for $^{19}$F magnetic resonance imaging (MRI). More particularly, the present invention relates to fluorinated fatty acid sulfonate derivatives, such as those derived by reaction of fluorinated fatty acids with sulfonated compounds such as taurine analogs or isethionic acid analogs, which offer improved water solubility and biocompatibility.

51 Claims, 1 Drawing Sheet

WATER SOLUBLE FLUORINATED FATTY ACID SULFONATE DERIVATIVES USEFUL AS MAGNETIC RESONANCE IMAGING AGENTS

DESCRIPTION

TECHNICAL FIELD

The present invention relates to improved imaging agents useful for $^{19}$F magnetic resonance imaging ($^{19}$F MRI). More particularly, the present invention relates to fluorinated fatty acid sulfonate derivatives, such as those obtained by reaction of fluorinated fatty acids with sulfonated compounds, such as taurine analogs or isethionic acid analogs, which are useful as $^{19}$F MRI agents.

BACKGROUND

Medical diagnostic imaging has evolved as an important non-invasive tool for the evaluation of pathological and physiological processes. Presently, nuclear magnetic resonance imaging (MRI) and computerized tomography (CT) are two of the most widely used imaging modalities. Although both MRI and CT can be performed without the administration of contrast agents, the ability of many contrast agents to enhance the visualization of internal tissues and organs, as well as soft-tissue differentiation, has resulted in their widespread use.

Magnetic imaging agents, and the imaging moieties they are comprised of, typically are substances that have magnetic properties which cause the brightening or darkening of a magnetic resonance image. At least four broad MRI methodologies are currently being pursued; these are proton MRI, paramagnetic metal MRI, nitroxyl spin label MRI, and $^{19}$F MRI.

Fluorine ($^{19}$F) MRI is still in the early stages of development. However, because of the 100% natural abundance of $^{19}$F and the complete absence of biological background, $^{19}$F MRI promises to be an important diagnostic imaging tool of the future. For example, previously disclosed fluorine-containing imaging agents include: perfluoro-tert-butyl containing organic compounds (W. J. Rogers, Jr., et al., U.S. Pat. No. 5,116,599 issued 1992, U.S. Pat. No. 5,234,680 issued 1993, and U.S. Pat. No. 5,324,504 issued 1994); fluoro-substituted benzene derivatives (P. Blaszkiewicz et al., U.S. Pat. No. 5,130,119 issued 1992; M. T. Kneller et al., U.S. Pat. No. 5,318,770 issued 1993 and U.S. Pat. No. 5,385,724 issued 1994; R. T. Dean, U.S. Pat. No. 4,612,185 issued 1986); fluorine containing nitroxyl compounds (M. D. Adams et al., U.S. Pat. No. 5,362,477 issued 1994); fluorinated metal-chelating compounds and chelates (Daikin Kogyo KK, JP 6-136347 published 1994; Asai et al., EP 592306, published 1994; Imigawa et al., EP 603403; Green Cross Corp, JP 5-186372 published 1993); fluorinated fullerenes (W. P. Cacheris et al., U.S. Pat. No. 5,248,498); fluorene-amine compounds (W. H. Moos, U.S. Pat. No. 4,960,815 issued 1990 and U.S. Pat. No. 5,081,304 issued 1992); N-methyl-glucamine salts (G. B. Hoey et al., U.S. Pat. No. 4,639,364 issued 1987 and U.S. Pat. No. 4,913,853 issued 1990); fluorocarbons (D. M. Long, WO 89/03693 published 1989); perfluoro crown ethers (J. A. Rubertone et al., U.S. Pat. No. 4,838,274 issued 1989); perfluoro dioxolanes (H. -N. Huang et al., U.S. Pat. No. 5,070,213 issued 1991); perfluoro tert-butyl aryl compounds (A. Krishnan et al., U.S. Pat. No. 5,401,493, issued 1995); and perfluoro tert-butyl containing steroids (T. S. Everett et al., U.S. Pat. No. 5,397,563, issued 1995).

The inventors postulated that the targeting properties of fatty acids might be combined with the MRI properties of $^{19}$F to yield useful imaging agents. However, preliminary experiments revealed that aqueous solutions of fluorinated fatty acids, such as perfluoro-t-butyl-pentadecanoate (e.g., $(CF_3)_3C—(CH_2)_{14}—COONa$), were found to be toxic when administered intravenously to rats. The pH of an aqueous solution of a fluorinated fatty acid salt (Na$^+$) is approximately 9.0. Upon adjusting the pH of the solution to near physiological values (pH about 7.5, thus forming the free acid), most of the fluorinated fatty acid precipitated out of solution. Therefore, the toxic effect was thought most likely to be due to precipitation of the fluorinated fatty acid in the blood.

The inventors subsequently discovered that the sulfonate derivatives of these fluorinated fatty acids (formed, by example, by reaction with an amino-sulfonic acid such as taurine, or with a hydroxy-sulfonic acid such as isethionic acid) may not only retain the useful fatty acid targeting properties and $^{19}$F magnetic resonance imaging properties of the simple fluorinated fatty acids, but also possess water solubilities which are relatively independent of pH. In effect, the acid function of the carboxylic acid group (with a pK$_a$ typically about 4.9) is replaced by a sulfonic acid group (with a pK$_a$ typically below about 2), thus offering improved water solubility and biocompatibility.

The salts of the fluorinated fatty acid sulfonate derivatives are water-soluble and will likely preferentially go to the kidneys. It can also be anticipated that, depending on the particular compound chosen as a contrast agent, and also its formulation, a good portion of the fluorinated fatty acid compounds go to the liver. For example, an emulsion may be prepared from a suitable oil and the desired fluorinated fatty acid sulfonate derivative (which may act as an emulsifier). Upon delivery to the liver, the amide or ester linkages of the fluorinated fatty acid sulfonates would be hydrolyzed. The freed fatty acids would then enter the fatty acid cycle; they would undergo enzymatic activation via mitochondrial, microsomal and peroxisomal carnitine acyltransferases and subsequently could be transported as acyl carnitines to the heart, where they would undergo β-oxidation (see, e.g., *Current Concepts in Carnitine Research*, A. Lee Carter, ed., CRC Press, 1992). Remaining fluorinated acetic acid or similar short-chain oxidation products would finally be excreted by the kidneys, possibly in the form of acyl carnitines.

SUMMARY OF THE INVENTION

The present invention relates to $^{19}$F magnetic resonance imaging agents of the formula M—L—J wherein M is a fluorinated imaging moiety, L is a fatty acid linker group, and J is a sulfonated moiety selected from the group of taurine-like moieties and isethionic acid-like moieties, and pharmacologically acceptable salts thereof. Preferred fluorinated imaging moieties, M, comprise at least one —CF$_3$ moiety. Other preferred fluorinated imaging moieties, M, comprise at least one —C(CF$_3$)$_3$ moiety. Preferred fatty acid linker groups, L, are derived from linear saturated fatty acids. Other preferred fatty acid linker groups, L, are derived from linear unsaturated or polyunsaturated fatty acids.

One group of preferred $^{19}$F magnetic resonance imaging agents comprise a taurine-like moiety as the sulfonated moiety, J, said taurine-like moiety derived from a compound of the formula HRN—(CH$_2$)$_s$—SO$_3$H, wherein R is —H or an alkyl, and s is an integer from 1 to 10. Another group of preferred $^{19}$F magnetic resonance imaging agents comprise an isethionic acid-like moiety as the sulfonated moiety, J, said isethionic acid-like moiety derived from a compound of the formula HO—$(CH_2)_s$—$SO_3H$, wherein s is an integer from 1 to 10.

Other preferred groups of $^{19}F$ magnetic resonance imaging agents may be represented by the following formulae:

(I) $C_pH_qF_r$—$C_xH_y$—$C(=O)$—$Q$—$C_sH_t$—$SO_3Z$ (II) $C_pF_r$—$C_xH_y$—$C(=O)$—$Q$—$C_sH_t$—$SO_3Z$ (III) $CF_3$—$(CH_2)_{x1}$—$C(=O)$—$Q$—$(CH_2)_s$—$SO_3Z$ (IV) $(CF_3)_3C$—$(CH_2)_{x2}$—$C(=O)$—$Q$—$(CH_2)_s$—$SO_3Z$ wherein (for formula I) p is an integer from 1 to 20; q is an integer from 1 to 40; r is an integer from 1 to 40 and wherein (for formula II) p is an integer from 1 to 20; r is an integer from 3 to 41; and wherein (for formulae I-IV) x is an integer from 0 to 25; y is an integer from 0 to 50; x1 is an integer from 0 to 25; x2 is an integer from 1 to 25; Q is NH or O; s is an integer from 1 to 10; t is an integer from 2 to 20; and Z is —H or a monovalent cation; with the proviso that if Q is O, then x and x1 are 1 or greater.

The present invention also pertains to compositions useful for $^{19}F$ magnetic resonance imaging which comprise the above $^{19}F$ magnetic resonance imaging agents, as well as methods of $^{19}F$ magnetic resonance imaging.

DETAILED DESCRIPTION

A. $^{19}F$ Magnetic Resonance Imaging Agents

Figure 1:
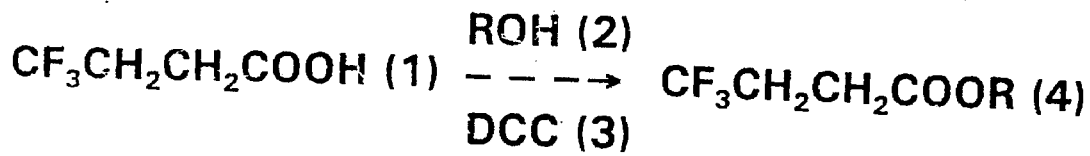
FIG. 1 is a flow chart that illustrates a synthetic route for the preparation of the $^{19}F$ magnetic resonance imaging agent $CF_3$—$CH_2CH_2$—$C(=O)NH$—$CH_2CH_2$—$SO_3Na$ of Example 1.
Figure 1:
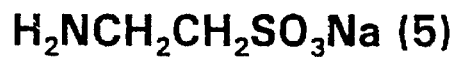
Figure 1:
Figure 2:
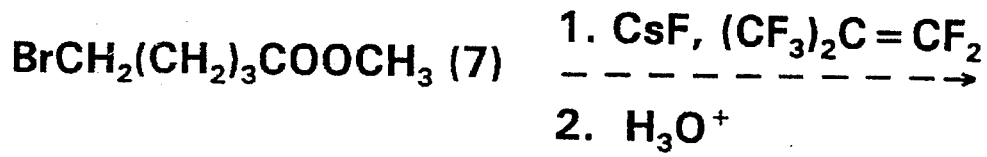
FIG. 2 is a flow chart that illustrates a synthetic route for the preparation of the $^{19}F$ magnetic resonance imaging agent $(CF_3)_3C$—$(CH_2)_4$—$C(=O)NH$—$CH_2CH_2$—$SO_3Na$ of Example 2.
Figure 2:
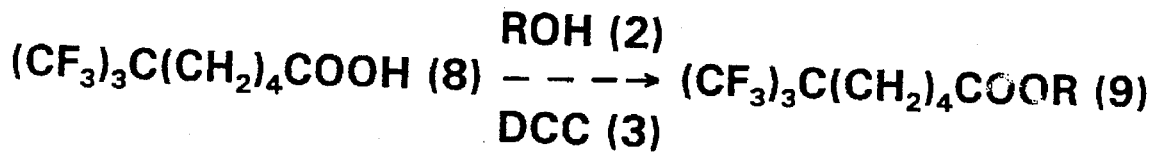
Figure 2:
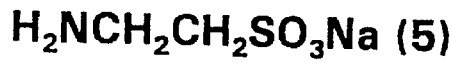
Figure 2:
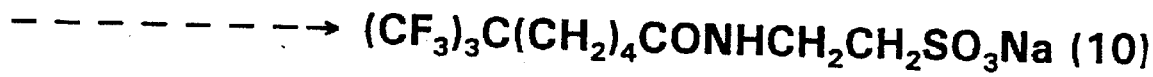

The present invention relates to imaging agents that enhance diagnostic images generated by fluorine magnetic resonance imaging ($^{19}F$ MRI). These $^{19}F$ MRI imaging agents may be considered to be fluorinated fatty acid sulfonate derivatives, and may be generally represented by the formula M—L—J, wherein M is a fluorinated imaging moiety, L is a fatty acid linker, and J is a sulfonated moiety.

As used herein, the term "fluorinated imaging moiety" (denoted M in the general formula M—L—J) relates to chemical moieties which comprise at least one fluorine atom. If the fluorinated imaging moiety comprises a plurality of fluorine atoms, it is preferred that the fluorine atoms be magnetically equivalent. As used herein, the term "magnetically equivalent" denotes atoms present in a moiety or compound which yield magnetic resonance signals of a sufficiently similar frequency that they form a single resonance peak as detected by typical diagnostic magnetic resonance imaging apparati (see, for example, Rogers et al., 1993, U.S. Pat. No. 5,234,680).

The simplest fluorinated imaging moiety is —F. Another group of fluorinated imaging moieties are the fluorohydrocarbyls (e.g., —$C_pH_qF_r$) wherein p is an integer from 1 to about 20, more preferably from 1 to about 15; and q and r are integers from 1 to about 40, more preferably from 1 to about 30. Examples of fluorohydrocarbyls include fluorinated aryl and fluorinated alkaryl groups, such as phenyls with substituents such as trifluoro methyl (—$CF_3$) and perfluoro-1H-1H-neopentyl (e.g., "PFNP", —$CH_2C(CF_3)_3$). Preferred fluorohydrocarbyls include para(PFNP)phenyl and meta,meta-bis(PFNP)phenyl.

Yet another group of fluorinated imaging moieties are the perfluorocarbyls (e.g., —$C_pF_r$), wherein p is an integer from 1 to about 20, more preferably from 1 to about 10, still more preferably from 1 to about 5; and r is an integer from 3 to about 41, more preferably from 3 to about 21, still more preferably from 3 to about 11. Preferred perfluorocarbyl imaging moieties are noncyclic.

Preferred fluorinated imaging moieties comprise at least three magnetically equivalent fluorine atoms (e.g., as provided by the trifluoromethyl group, —$CF_3$). Other preferred fluorinated imaging moieties comprise at least nine magnetically equivalent fluorine atoms (e.g., as provided by the perfluoro-tert-butyl group, —$C(CF_3)_3$).

As used herein, the term "fatty acid linker" (denoted L in the general formula M—L—J) relates to divalent chemical moieties which are derived from fatty acids. The term "fatty acid" is used herein in the conventional sense to mean an organic compound which consists of a hydrocarbon chain possessing a terminal carboxylic acid group (e.g., —COOH).

The term "hydrocarbon chain" is used herein in the conventional sense to mean a non-cyclic radical consisting only of carbon and hydrogen (e.g., —$C_xH_y$), which may be linear or branched, but is preferably linear.

The term "hydrocarbon chain length" is used herein in the conventional sense to refer to the number of carbon atoms in the entire fatty acid, including the carbon atom of the carboxylic acid moiety (e.g., stearic acid, $CH_3(CH_2)_{16}COOH$ has a chain length of 18 denoted C-18). Note that methanoic acid (e.g., formic acid, HCOOH, C-1) is often referred to as the simplest member of the fatty acid family, and in this instance the so-called hydrocarbon chain consists only of —H.

Typical fatty acids have hydrocarbon chain lengths from one (e.g., methanoic acid, HCOOH) to about 25. Common fatty acids such as ethanoic acid (e.g., acetic acid, $CH_3COOH$, C-2), propanoic acid (e.g., propionic acid, $CH_3CH_2COOH$, C-3), and butanoic acid (e.g., butyric acid, $CH_3CH_2CH_2COOH$, C-4) are important in metabolism. Long-chain fatty acids (e.g., fatty acids with chain lengths greater than about 8), which are also important in metabolism, most commonly occur as constituents of certain lipids, notably glycerides, phospholipids, sterols, and waxes, in which they are esterified with alcohols. Long-chain fatty acids typically have an even number of carbon atoms, that is, have even numbered chain lengths. Examples of common long-chain fatty acids include tetradecanoic acid (e.g., myristic acid, $CH_3(CH_2)_{12}COOH$, C-14), hexadecanoic acid (e.g., palmitic acid, $CH_3(CH_2)_{14}COOH$, C-16), and octadecanoic acid (e.g., stearic acid, $CH_3(CH_2)_{16}COOH$, C-18).

Fatty acids may be referred to as "saturated", "unsaturated", or "polyunsaturated", depending on the number of double and/or triple carbon-carbon bonds (e.g., —CH=CH— or —C≡C—, respectively) present in the hydrocarbon chain. Saturated fatty acids are fatty acids which are fully saturated and possess no carbon-carbon double bonds. Unsaturated fatty acids are fatty acids which possess only one carbon-carbon double bond, or, alternatively, only one carbon-carbon triple bond. Polyunsaturated fatty acids are fatty acids which possess more than one unsaturated carbon-carbon bond, that is, a plurality of carbon-carbon double-and/or triple bonds. An example of an unsaturated fatty acid is oleic acid (cis-octodec-9-enoic acid, $CH_3(CH_2)_6CH_2CH=CHCH_2(CH_2)_6COOH$, C-18), which possesses one carbon-carbon double bond. An example of a polyunsaturated fatty acid is linoleic acid (trans,trans-octadeca-9,12-dienoic acid, $CH_3(CH_2)_3CH_2$—CH=CH—$CH_2$—CH=CH—$CH_2(CH_2)_6COOH$, C-18) and linolenic acid (trans,trans,trans-octadeca-9,12,15-trienoic acid, $CH_3CH_2$—CH=CH—$CH_2$—CH=CH—$CH_2$—CH=CH—$CH_2(CH_2)_6COOH$, C-18).

Fatty acid linkers, therefore, are diradical moieties derived from fatty acids. A preferred group of fatty acid linkers are those of the general formula —$C_xH_y$—C(=O)—, wherein x is an integer from 0 to about 25, more preferably from 0 to about 20. For example, one fatty acid linker derived from stearic acid might be —$(CH_2)_{17}C(=O)$—.

As used herein, the term "sulfonated moiety" (denoted J in the general formula M—L—J) relates to chemical moieties which comprise an organic group, a reactive functional group (for example, an amino group —NHR or a hydroxyl group —OH) and a sulfonic acid, sulfonate, sulfuric acid, or sulfate group (—$SO_3H$, —$SO_3^-$, —$OSO_3H$, or —$OSO_3^-$, respectively). Preferred sulfonated moieties are the amino-alkane-sulfonic acids, amino-alkane-sulfonates, amino-alkyl-sulfuric acids, amino-alkyl-sulfates, hydroxy-alkane-sulfonic acids, hydroxy-alkane-sulfonates, hydroxy-alkyl-sulfuric acids, and hydroxy-alkyl-sulfates. More preferred sulfonated moieties are taurine-like moieties and isethionic acid-like moieties.

The term "taurine-like moiety" as used herein relates to chemical moieties which resemble in structure the organic compound taurine (e.g., 2-aminoethanesulfonic acid, $H_2N$—$CH_2$—$CH_2$—$SO_3H$), that is, taurine analogs. More particularly, the term taurine-like moiety relates to compounds and radicals comprising an amino group, preferably a terminal amino group (—NHR), a sulfonic acid or sulfonate group (—$SO_3H$ or —$SO_3^-$, respectively), and a non-cyclic hydrocarbyl diradical (—$C_tH_r$—) therebetween, and may be represented by the general formula HRN—$C_tH_r$—$SO_3Z$, wherein Z is —H or a monovalent cation, and s and t are as defined below. R is preferably —H, thus yielding an unsubstituted amino group, but R may also be a hydrocarbyl group, more preferably an alkyl group, still more preferably an alkyl group with from 1 to 5 carbon atoms, yet more preferably a methyl or ethyl group, most preferably a methyl group, thus yielding a mono-substituted amino group.

The term "isethionic acid-like moiety" as used herein relates to chemical moieties which resemble in structure the organic compound isethionic acid (e.g., 2-hydroxyethanesulfonic acid, HO—$CH_2CH_2$—$SO_3H$), that is, isethionic acid analogs. More particularly, the term isethionic acid-like moiety relates to compounds and radicals comprising a hydroxyl group, preferably a terminal hydroxyl group (—OH), a sulfonic acid or sulfonate group (—$SO_3H$ or —$SO_3^-$, respectively), and a non-cyclic hydrocarbyl diradical (—$C_tH_r$—) therebetween, and may be represented by the general formula HO—$C_tH_r$—$SO_3Z$, wherein Z is —H or a monovalent cation, and s and t are as defined below.

The terms "amino-alkyl-sulfuric acid moiety" and "amino-alkyl-sulfate moiety" as used herein relate to compounds and radicals comprising an amino group (—NHR), a sulfuric acid or sulfate group (—$OSO_3H$ or —$OSO_3^-$, respectively) and a non-cyclic hydrocarbyl diradical (—$C_tH_r$) therebetween, and may be represented by the general formula HRN—$C_tH_r$—$OSO_3Z$, wherein Z is —H or a monovalent cation, R is as defined above, and s and t are as defined below.

Similarly, the terms "hydroxy-alkyl-sulfuric acid moiety" and "hydroxy-alkyl-sulfate moiety" as used herein relate to compounds and radicals comprising a hydroxyl group (—OH), a sulfuric acid or sulfate group (—$OSO_3H$ or —$OSO_3^-$, respectively) and a non-cyclic hydrocarbyl diradical (—$C_tH_r$—) therebetween, and may be represented by the general formula HO—$C_tH_r$—$OSO_3Z$, wherein Z is —H or a monovalent cation, and s and t are as defined below.

In the above formulae, s is an integer from 1 to about 10, more preferably from about 2 to about 5, still more preferably from about 2 to about 4, yet more preferably 2 or 3; with the proviso that s is greater than 1 for the sulfuric acid or sulfate compounds. The hydrocarbyl group may be linear or branched, but is preferably linear. The hydrocarbyl group may be fully saturated, partially unsaturated, or fully unsaturated (but is preferably fully saturated), and t may therefore vary from 2 to 20 according to the choice of s and the degree of unsaturation. Preferred hydrocarbyl groups include —$(CH_2)_s$—.

A preferred group of taurine-like moieties are the fully saturated, unsubstituted, linear analogs (e.g., $H_2N$—$(CH_2)_s$—$SO_3H$), and a preferred group of isethionic acid-like moieties are the fully saturated linear analogs (e.g., HO—$(CH_2)_s$—$SO_3H$), wherein s is an integer from 1 to 10, more preferably from 2 to 5, still more preferably from 2 to 4, yet more preferably 2 or 3, most preferably 2 (e.g., taurine or isethionic acid themselves).

The term "salt" as used herein denotes ionic compounds involving suitable metal or organic ions. Suitable pharmacologically acceptable salts may contain, for example, metal ions, for example, alkali and alkaline earth cations, preferably $Na^+$, $K^+$, $Mg^{+2}$, and $Ca^{+2}$, more preferably $Na^+$ and $K^+$, and organic ions, for example, stable cationic species such as N-methylglucamine ("meglumine") cation, and tris (hydroxymethyl)amino methane ("TRIS") cation. The $^{19}F$ magnetic resonance imaging agents of the present invention all possess a sulfonic acid or sulfonate group (—$SO_3H$ or —$SO_3^-$, respectively, both generalized by the formula —$SO_3Z$, wherein Z is —H or a cation with (+1) charge) or a sulfuric acid or sulfate group (—$OSO_3H$ or —$OSO_3^-$, both generalized by the formula —$OSO_3Z$, wherein Z is —H or a cation with (+1) charge). It may be preferable to obtain and use the imaging agents in their salt form.

It is useful to consider the $^{19}F$ magnetic resonance imaging agents of the present invention as fluorinated fatty acids which have been reacted with a sulfonated compound, such as a taurine-like compound or an isethionic acid-like compound, to yield a fluorinated fatty acid sulfonic acid or sulfonate derivative which possesses an amide or ester linkage, respectively.

Two groups of the $^{19}F$ magnetic resonance imaging agents of the present invention may be represented by the following general formulae:

(I) $C_pH_qF_r$—$C_xH_y$—C(=O)—Q—$C_sH_t$—$SO_3Z$ (II) 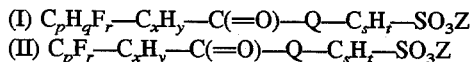

wherein the fluorinated moieties, $C_pH_qF_r$ and $C_pF_r$, the fatty acid portion, $C_xH_y$, and the taurine-like portion $C_sH_t$ are of the form discussed above, Q is NH (yielding an amide linkage) or O (yielding an ester linkage), and Z is —H or a pharmacologically acceptable cation with (+1) charge. Owing to the reactivity of the esters (when Q is O) under aqueous conditions, x is 1 or greater, more preferably 2 or greater.

Two smaller groups of preferred $^{19}F$ magnetic resonance imaging agents of the present invention may be represented by the following general formulae:

(III) $CF_3$—$(CH_2)_{x1}$—C(=O)—Q—$CH_2CH_2$—$SO_3Z$ (IV) 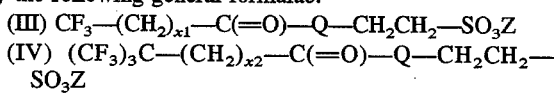

wherein x1 is an integer from 0 to about 25, preferably from 0 to about 20; x2 is an integer from 1 to about 25, preferably from about 1 to about 20; and Q and Z are as defined above. One group of preferred imaging agents has values of x1 which are 0, 1, 2, 4, 10, 12, 14, and 16, while another group of preferred imaging agents has values of x2 which are 1, 2, 4, 10, 12, 14, and 16. Again, owing to the reactivity of the esters (when Q is O), x1 is 1 or greater, more preferably 2 or greater (for example, the trifluoroacetic acid esters are likely too reactive and not stable under aqueous conditions).

B. Methods of Preparation

As discussed above, it is useful to consider the $^{19}$F magnetic resonance imaging agents of the present invention as fluorinated fatty acids which have been reacted with a sulfonated compound, such as a taurine-like compound or an isethionic acid-like compound, to yield a fluorinated fatty acid sulfonic acid or sulfonate derivative which possesses an amide or ester linkage, respectively, since this reflects a simple method for their preparation.

Such a synthesis begins with a fluorinated fatty acid, which may be purchased or synthesized. Fluorinated fatty acids may be synthesized by any of a variety of known methods. For example, trifluorobutanoic acid may be synthesized from (1,1,1-trifluoromethyl) propyl chloride via a Grignard reaction according to E. T. McBee and A. Truchan (J. Amer. Chem. Soc., 1948, Vol. 70, p.2911).

In another method, the haloderivative of a fatty acid, which may be purchased or synthesized by any of a variety of known methods, may be derivatized to possess the perfluoro-tert-butyl group according to the method of Roger et al. (1993, U.S. Pat. No. 5,234,680). For example, the haloderivative may be reacted with perfluoroisobutylene and cesium fluoride in monoglyme ($CH_3O—CH_2CH_2—OCH_3$).

The next step in the preparation of the $^{19}$F magnetic resonance imaging agents of the present invention would involve the formation of an amide or ester linkage between the fatty acid and the amino group of the taurine-like moiety.

For those $^{19}$F magnetic resonance imaging agents which comprise an amide linkage, this next step may easily be achieved by first forming the active ester of the fatty acid, for example, by reacting the fatty acid with a suitable hydroxy-containing compound, for example, 1-hydroxybenzotriazole or N-hydroxysuccinimide, in the presence of a suitable base, and subsequently reacting the active ester with a taurine-like moiety (or its salt) in a suitable solvent, such as dimethyl-formamide.

For those $^{19}$F magnetic resonance imaging agents which comprise an ester linkage, the above-mentioned next step may easily be achieved by simply mixing the fluorinated fatty acid with an isethionic acid-like moiety (or its salt) in a suitable solvent, such as dimethylformamide (DMF) with pyridine in the presence of 1,3-dicyclohexylcarbodiimide (DCC).

Taurine may be purchased, for example, from Aldrich. Taurine salts may be purchased or prepared from taurine by reaction with a suitable base, such as sodium hydroxide. Taurine-like compounds may be purchased or synthesized by any of a variety of known methods; for example, N-methyl taurine is commercially available, and other N-substituted taurines may be prepared from taurine by any of a variety of known methods. Isethionic acid may be purchased, for example, from Aldrich. Isethionic acid-like compounds may be purchased or synthesized by any of a variety of known methods.

C. Methods of Imaging

The methods of MRI are well known in the art. See, inter alia, The Contrast Media Manual, (1992, R. W. Katzberg, Williams and Wilkins, Baltimore, Md.), especially Chapter 13 ("Magnetic Resonance Contrast Agents").

Typically, an effective amount of an imaging agent formulation comprising the $^{19}$F magnetic resonance imaging agent and a pharmaceutically acceptable carrier is administered to the patient, and the patient, or a portion of the patient, is imaged. The term "effective amount", as used herein, denotes a non-toxic amount sufficient to enhance or alter the MRI image obtained, more particularly, an amount which permits better visualization of the organs and/or tissues being imaged.

Preferably the patient is a mammal; most preferably the patient is a human.

The $^{19}$F magnetic resonance imaging agents of the present invention may be variously administered by any suitable route, including, for example, orally, for imaging of the upper gastrointestinal tract; rectally, for imaging of the lower gastrointestinal tract including the colon; nasally, for imaging of the nasal and communicating passages; vaginal, for imaging of the fallopian tubes and communicating passages; parenteral (including subcutaneous, intramuscular, intravenous, intradermal and pulmonary), for imaging of internal organs, tissues, tumors, and the like. It will be appreciated that the preferred route will vary with the organs or tissues to be imaged. Preferred routes of administration include parenteral and oral, more preferably intravenous.

While it is possible for the imaging agent to be administered alone, it is preferable to present it as a pharmaceutical formulation comprising at least one imaging agent compound, together with one or more pharmaceutically acceptable carriers, such as diluents or excipients which may include, for example, fillers, extenders, wetting agents, disintegrants, surface-active agents, or lubricants, depending on the nature and mode of administration and the dosage forms. Each carrier must be "acceptable" in the sense of being compatible with the other ingredients of the formulation and not injurious to the patient. The pharmaceutical formulation may optionally include other diagnostic or therapeutic agents. Techniques and formulations may be found, for example, in Remington's Pharmaceutical Sciences, Mack Publishing Co., Easton, Pa. (latest edition).

Formulations of the present invention suitable for oral administration may be presented as an aqueous solution. Alternatively, formulations can be administered as capsules, cachets or tablets, each containing a predetermined amount of the imaging agent; powder; granules; or paste.

Formulations suitable for parenteral administration include aqueous isotonic sterile injection solutions which may contain anti-oxidants, buffers, bacteriostats and solutes which render the formulation isotonic with the blood of the intended recipient; and aqueous sterile suspensions which may include suspending agents and thickening agents, and liposomes or other microparticulate systems which are designed to target the compound to one or more tissues or organs.

The formulations may be presented in unit-dose or multi-dose sealed containers, for example, ampules and vials, and may be stored in a freeze-dried (lyophilized) condition requiring only the addition of the sterile liquid carrier, for example water, for injections immediately prior to use. Extemporaneous injection solutions and suspensions may be prepared from sterile powders, granules or tablets.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents.

The $^{19}$F magnetic resonance imaging agents of the present invention may also be presented for use in the form of veterinary formulations, which may be prepared, for example, by methods that are conventional in the art.

For effective $^{19}$F MRI, dosages of the $^{19}$F magnetic resonance imaging agent will depend on the spin density, flow (diffusion and perfusion), susceptibility, and relaxivity (T1 and T2) of the imaging agent formulation. Dosages of $^{19}$F containing imaging agents may be conveniently calculated in milligrams of $^{19}$F per kilogram of patient (abbreviated as mg $^{19}$F/kg). For example, for parenteral administration, typical dosages may be from about 50 to about 1000 mg $^{19}$F/kg, more preferably from about 100 to about 500 mg $^{19}$F/kg.

For methods of continuous administrations (e.g., intravenous), suitable rates of administration are known in the art. Typical rates of administration are about 0.5 to 5 mL of formulation per second, more preferably about 1–3 mL/s. Imaging may begin before or after commencing administration, continue during administration, and may continue after administration.

It will be appreciated that dosages, dosage volumes, formulation concentrations, rates of administration, and imaging protocols will be individualized to the particular patient and the examination sought, and may be determined by an experienced practitioner. Guidelines for selecting such parameters are known in the art (see, inter alia, Katzberg, 1992, supra).

The usefulness and efficiency of chemical compounds as contrast agents depends on their ability to exhibit a predictable and desirable biodistribution and metabolism in vivo. Their behavior in vivo depends on parameters such as molecular weight, charge, osmolality, hydrophobicity, partition coefficient, susceptibility to metabolic breakdown, and tissue or organ targeting efficiency. In order to improve their solubility and/or biodistribution, many contrast agents are used in conjunction with delivery systems such as emulsions, liposomes, and microparticles.

D. Examples

Example 1

Preparation of $CF_3$—$CH_2CH_2$—$C(=O)NH$—$CH_2CH_2$—$SO_3Na$

A solution of trifluorobutanoic acid, compound (1) ($CF_3CH_2CH_2CO_2H$, MW=142, 1.24 g, 8.7 mmol; obtained from Narchem) was dissolved in 10 mL of dimethylformamide. 1-Hydroxybenzotriazole, compound (2) ($C_6H_5N_3O$, MW=135, 1.30 g, 9.6 mmol; obtained from Aldrich, contains approximately 5% water) was dried azeotropically by first dissolving in pyridine followed by the removal of pyridine under vacuum. The residue was dissolved in 10 mL of dimethylformamide. The sodium salt of taurine, compound (5), was prepared by reaction of taurine ($H_2NCH_2CH_2SO_3H$; obtained from Aldrich) with an equimolar amount of aqueous sodium hydroxide followed by lyophilization and drying in vacuo. The trifluorobutanoic acid (1) solution was added to the 1-hydroxybenzotriazole (2) solution with stirring. A solution of 1,3-dicyclohexylcarbodiimide, compound (3) (DCC, $C_6N_{11}N=C=N$—$C_6H_{11}$, MW=206, 2.08 g, 10 mmol; obtained from Aldrich) in 5 mL dimethylformamide was subsequently added to the mixture. After 5 min, the N,N'-dicyclohexylurea started to precipitate out, indicating the formation of the active ester, compound (4). Reaction was allowed to proceed for 1 hour, after which the taurine sodium salt (5) ($H_2NCH_2CH_2SO_3Na$, MW=147, 1.25 g, 8.5 mmol) was added with vigorous stirring. The taurine sodium salt was carefully dissolved with the aid of a sonication water bath. The mixture was stirred approximately 12 hours, and the precipitate removed by filtration and then triturated with water. The water insoluble solids were removed by filtration. Most of the water and dimethylformamide was removed from the filtrate under reduced pressure. The dimethylformamide containing residue was diluted with 50 mL ethyl ether and the gel-like solid was centrifuged, and the resulting solid washed with ethyl ether (3×30 mL) and dried in vacuo to yield the desired compound (6) (1.94 g, 93%) yield. The $^1$H NMR spectrum in $D_2O$ showed the following resonances relative to HOD: δ 3.55 (t, 2H, $CH_2$), 3.10 (t, 2H, $CH_2$), 2.50 (m, 4H, $CH_2$).

Example 2

Preparation of $(CF_3)_3C$—$(CH_2)_4$—$C(=O)NH$—$CH_2CH_2$—$SO_3Na$

Perfluoro-tert-butyl valeric acid, compound (8) ($(CF_3)_3C(CH_2)_4CO_2H$, MW=320, 7.1 g, 22.2 mmol; prepared from methyl 5-bromopentanoate (7) (Aldrich) and perfluoroisobutylene gas (Flura Corporation) according to the procedure of Rogers et al., 1993, U.S. Pat. No. 5,234,680) was dissolved in 25 mL of dimethylformamide. 1-Hydroxybenzotriazole, compound (2) ($C_6H_5N_3O$, MW=135, 3.36 g, 25 mmol; Aldrich), was dried azeotropically by first dissolving it in pyridine followed by removal of the pyridine under vacuum. The residue was dissolved in 25 mL of dimethylformamide. The sodium salt of taurine, compound (5), was prepared by reaction of taurine $H_2NCH_2CH_2SO_3H$, MW=125, 3.22 g, 25.78 mmol (Aldrich) with an equimolar amount of aqueous sodium hydroxide followed by lyophilization and drying in vacuo. The perfluoro-tert-butyl valeric acid (8) solution was added to the 1-hydroxybenzotriazole (2) solution at room temperature with stirring. A solution of 1,3-dicyclohexylcarbodiimide, compound (3) (DCC, $C_6H_{11}N=C=NC_6H_{11}$, MW=206, 5.15 g, 25 mmol, from Aldrich) in 50 mL of dimethylformamide was subsequently added to the mixture. The mixture was stirred for 1 hour, at which time the N,N'-dicyclohexylurea had precipitated out, indicating the formation of the active ester, compound (9). The taurine salt (5) was then added with vigorous stirring, and the mixture stirred for approximately 12 hours. The mixture was warmed to 70° C. in an oil bath for 30 minutes and then cooled. The gel-like solid which had precipitated was filtered and triturated with 75 mL of isopropanol at 70° C. Upon cooling, a crystalline precipitate formed which was removed by filtration, washed with ethyl ether and then dried in vacuo. Thin-layer chromatography indicated that unreacted taurine salt and 1-hydroxybenzotriazole impurities remained. The solid was triturated with 50 mL of methanol and the insoluble taurine (0.425 g) was removed by filtration. Methanol was evaporated from the filtrate in vacuo and the residue diluted with 50 mL ethyl ether. The essentially pure solid product, compound (10), was filtered off and dried in vacuo (5.6 g, 56.2% yield); $^1$H—NMR indicated greater than 95% purity with 3–4% 1-hydroxybenzotriazole. The $^1$H—NMR spectrum in $D_2O$ showed the following resonances relative to HOD: δ 3.55 (t, 2H, $CH_2$) 3.10 (t, 2H, $CH_2$) 2.0–2.3 (m, 4H, $CH_2$) 1.55 (s, broad, 4H, $CH_2$); $^{19}$F spectrum in the same solvent showed a single resonance at −66.40 (s, 9F) ppm relative to freon.

Example 3

In Vivo $^{19}$F Magnetic Resonance Imaging

Imaging agents for $^{19}$F MRI are prepared as described in Examples 1 and 2 are suspended in a pharmaceutically acceptable carrier such as sterile water or physiological saline. Fluorine ($^{19}$F) imaging is carried out using standard procedures and commercially available equipment. Fluorine imaging may be performed with the following parameters: TR=1 second, TE=18 milliseconds, image data matrix=64× 64, NEX=32, FOV=128 nm. Fluorine MRI is done before and after administration of the contrast agent. Proton MRI may be used to provide anatomic markers for assessment of the fluorine images. Imaging agent dosages may be calculated as described in Example 4.

Example 4

Imaging Agent Dosage Calculations

Imaging dosages will depend on the solubility of the imaging agent, the route of administration, the carrier vehicle, the site to be imaged and the method of imaging. Dosages of $^{19}$F containing imaging agents may be conveniently calculated in milligrams of $^{19}$F per kilogram of patient (abbreviated as mg $^{19}$F/kg). For example, for parenteral administration, typical dosages may be from about 100 mg $^{19}$F/kg to about 500 mg $^{19}$F/kg. For the $^{19}$F MRI agent described in Example 1 ($CF_3$—$CH_2CH_2$—C(=O)NH—$CH_2CH_2$—$SO_3Na$, which has a molecular weight of 271 and which contains 3 fluorine atoms), the fluorine content is 21% by weight. For a typical 70 kg patient, a dosage of from about 7 g to about 35 g of $^{19}$F, or from about 33 to 165 g of this agent may be suitable. Similarly, for the $^{19}$F MRI agent described in Example 2 $((CF_3)_3C$—$(CH_2)_4$—C(=O)NH—$CH_2CH_2$—$SO_3Na$, which has a molecular weight of 449 and which contains 9 fluorine atoms), the fluorine content is 38.1% by weight. In this case, for a typical 70 kg patient, a dosage of from about 7 g to about 35 g of $^{19}$F, or from about 18 to 90 g of this agent may be suitable.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the invention as described by the appended claims.

What is claimed is:

1. A $^{19}$F magnetic resonance imaging agent of the formula M—L—J wherein M is a fluorinated imaging moiety, L is a fatty acid linker group, and J is a sulfonated moiety selected from the group of taurine-like moieties and isethionic acid-like moieties; or a pharmacologically acceptable salt thereof.

2. The $^{19}$F magnetic resonance imaging agent of claim 1 wherein said sulfonated moiety, J, is a taurine-like moiety.

3. The $^{19}$F magnetic resonance imaging agent of claim 1 wherein said sulfonated moiety, J, is an isethionic acid-like moiety.

4. The $^{19}$F magnetic resonance imaging agent of claim 1 wherein said fluorinated imaging moiety, M, comprises at least one —$CF_3$ moiety.

5. The $^{19}$F magnetic resonance imaging agent of claim 1 wherein said fluorinated imaging moiety, M, comprises at least one —$C(CF_3)_3$ moiety.

6. The $^{19}$F magnetic resonance imaging agent of claim 1 wherein said fatty acid linker group, L, is derived from a linear saturated fatty acid.

7. The $^{19}$F magnetic resonance imaging agent of claim 1 wherein said fatty acid linker group, L, is derived from a linear unsaturated or polyunsaturated fatty acid.

8. The $^{19}$F magnetic resonance imaging agent of claim 1 wherein said sulfonated moiety, J, is a taurine-like moiety which is derived from a compound of the formula HRN—$(CH_2)_s$—$SO_3H$, wherein R is —H or an alkyl, and s is an integer from 1 to 10.

9. The $^{19}$F magnetic resonance imaging agent of claim 8 wherein s is 2 or 3.

10. The $^{19}$F magnetic resonance imaging agent of claim 1 wherein said sulfonated moiety, J, is an isethionic acid-like moiety which is derived from a compound of the formula HO—$(CH_2)_s$—$SO_3H$, wherein s is an integer from 1 to 10.

11. The $^{19}$F magnetic resonance imaging agent of claim 10 wherein s is 2 or 3.

12. The $^{19}$F magnetic resonance imaging agent of claim 1, which is represented by the general formula:

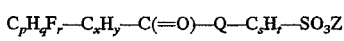

wherein p is an integer from 1 to 20; q is an integer from 1 to 40; r is an integer from 1 to 40; x is an integer from 0 to 25; y is an integer from 0 to 50; Q is NH or O; s is an integer from 1 to 10; t is an integer from 2 to 20; and Z is —H or a monovalent cation; with the proviso that if Q is O, then x is 1 or greater.

13. The $^{19}$F magnetic resonance imaging agent of claim 12, wherein the —$C_pH_qF_r$ group comprises an aryl or alkaryl moiety.

14. The $^{19}$F magnetic resonance imaging agent of claim 12, wherein the —$C_pH_qF_r$ group comprises a phenyl moiety with at least one perfluoro-1H-1H-neopentyl substituent.

15. The $^{19}$F magnetic resonance imaging agent of claim 1, which is represented by the general formula:

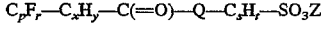

wherein p is an integer from 1 to 20; r is an integer from 3 to 41; x is an integer from 0 to 25; y is an integer from 0 to 50; Q is NH or O; s is an integer from 1 to 10; t is an integer from 2 to 20; and Z is —H or a monovalent cation; with the proviso that if Q is O, then x is 1 or greater.

16. The $^{19}$F magnetic resonance imaging agent of claim 15, which is represented by the general formula:

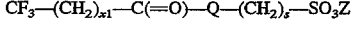

wherein x1 is an integer from 0 to 25; Q is NH or O; and s is an integer from 1 to 10; and Z is —H or a monovalent cation; with the proviso that if Q is O, then x1 is 1 or greater.

17. The $^{19}$F magnetic resonance imaging agent of claim 16, wherein Q is NH.

18. The $^{19}$F magnetic resonance imaging agent of claim 16, wherein Q is O.

19. The $^{19}$F magnetic resonance imaging agent of claim 16, wherein s is 2 or 3.

20. The $^{19}$F magnetic resonance imaging agent of claim 16, wherein x1 is 0, 1, 2, 4, 10, 12, 14, or 16, with the proviso that if Q is O, then x1 is not 0.

21. The $^{19}$F magnetic resonance imaging agent of claim 15, which is represented by the general formula:

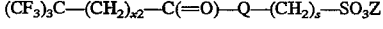

wherein x2 is an integer from 1 to 25; Q is NH or O; and s is an integer from 1 to 10; and Z is —H or a monovalent cation.

22. The $^{19}$F magnetic resonance imaging agent of claim 21, wherein Q is NH.

23. The $^{19}$F magnetic resonance imaging agent of claim 21, wherein Q is O.

24. The $^{19}$F magnetic resonance imaging agent of claim 21, wherein s is 2 or 3.

25. The $^{19}$F magnetic resonance imaging agent of claim 21, wherein x2 is 1, 2, 4, 10, 12, 14, or 16.

26. A composition useful for $^{19}$F magnetic resonance imaging, said composition comprising an effective amount of a $^{19}$F magnetic resonance imaging agent or a pharmacologically acceptable salt thereof, said imaging agent represented by the formula M—L—J wherein M is a fluorinated imaging moiety, L is a fatty acid linker group, and J is a sulfonated moiety selected from the group of taurine-like moieties and isethionic acid-like moieties; and a pharmaceutically acceptable carrier.

27. A method of $^{19}$F magnetic resonance imaging comprising the steps:

(a) administering to a patient an effective amount of a $^{19}$F magnetic resonance imaging agent or a pharmacologically acceptable salt thereof, said imaging agent represented by the formula M—L—J wherein M is a fluorinated imaging moiety, L is a fatty acid linker group, and J is a sulfonated moiety selected from the group of taurine-like moieties and isethionic acid-like moieties; and (b) acquiring an MR image of at least a portion of the patient while the $^{19}$F magnetic resonance imaging agent is present in the patient.

28. The method of claim 27, wherein said sulfonated moiety, J, is a taurine-like moiety.

29. The method of claim 27, wherein said sulfonated moiety, J, is an isethionic acid-like moiety.

30. The method of claim 27, wherein said fluorinated imaging moiety, M, comprises at least one —CF$_3$ moiety.

31. The method of claim 30, wherein said fluorinated imaging moiety, M, comprises at least one —C(CF$_3$)$_3$ moiety.

32. The method of claim 27, wherein said fatty acid linker group, L, is derived from a linear saturated fatty acid.

33. The method of claim 27, wherein said fatty acid linker group, L, is derived from a linear unsaturated or polyunsaturated fatty acid.

34. The method of claim 27, wherein said sulfonated moiety, J, is a taurine-like moiety which is derived from a compound of the formula HRN—(CH$_2$)$_s$—SO$_3$H, wherein R is H or an alkyl, and s is an integer from 1 to 10.

35. The method of claim 34, wherein s is 2 or 3.

36. The method of claim 27, wherein said sulfonated moiety, J, is an isethionic acid-like moiety which is derived from a compound of the formula HO—(CH$_2$)$_s$—SO$_3$H, wherein s is an integer from 1 to 10.

37. The method of claim 36, wherein s is 2 or 3.

38. The method of claim 27, wherein said $^{19}$F magnetic resonance imaging agent is represented by the general formula:

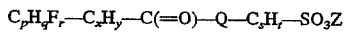

$$C_pH_qF_r—C_xH_y—C(=O)—Q—C_sH_t—SO_3Z$$

wherein p is an integer from 1 to 20; q is an integer from 1 to 40; r is an integer from 1 to 40; x is an integer from 0 to 25; y is an integer from 0 to 50; Q is NH or O; s is an integer from 1 to 10; t is an integer from 2 to 20; and Z is H or a monovalent cation; with the proviso that if Q is O, then x is 1 or greater.

39. The method of claim 38, wherein the —C$_p$H$_q$F$_r$ group comprises an aryl or alkaryl moiety.

40. The method of claim 38, wherein the —C$_p$H$_q$F$_r$ group comprises a phenyl moiety with at least one perfluoro-1H-1H-neopentyl substituent.

41. The method of claim 38, wherein said $^{19}$F magnetic resonance imaging agent is represented by the general formula:

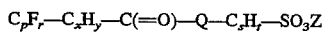

$$C_pF_r—C_xH_y—C(=O)—Q—C_sH_t—SO_3Z$$

wherein p is an integer from 1 to 20; r is an integer from 3 to 41; x is an integer from 0 to 25; y is an integer from 0 to 50; Q is NH or O; s is an integer from 1 to 10; t is an integer from 2 to 20; and Z is H or a monovalent cation; with the proviso that if Q is O, then x is 1 or greater.

42. The method of claim 41, wherein said $^{19}$F magnetic resonance imaging agent is represented by the general formula:

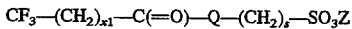

$$CF_3—(CH_2)_{x1}—C(=O)—Q—(CH_2)_s—SO_3Z$$

wherein x1 is an integer from 0 to 25; Q is NH or O; and s is an integer from 1 to 10; and Z is H or a monovalent cation; with the proviso that if Q is O, then x1 is 1 or greater.

43. The method of claim 42, wherein Q is NH.

44. The method of claim 42, wherein Q is O.

45. The method of claim 42, wherein s is 2 or 3.

46. The method of claim 42, wherein x1 is 0, 1, 2, 4, 10, 12, 14, or 16, with the proviso that if Q is O, then x1 is not 0.

47. The method of claim 41, wherein said $^{19}$F magnetic resonance imaging agent is represented by the general formula:

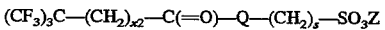

$$(CF_3)_3C—(CH_2)_{x2}—C(=O)—Q—(CH_2)_s—SO_3Z$$

wherein x2 is an integer from 1 to 25; Q is NH or O; and s is an integer from 1 to 10; and Z is H or a monovalent cation.

48. The method of claim 47, wherein Q is NH.

49. The method of claim 47, wherein Q is O.

50. The method of claim 47, wherein s is 2 or 3.

51. The method of claim 47, wherein x2 is 1, 2, 4, 10, 12, 14, or 16.

* * * * *